United States Patent
Basey et al.

(10) Patent No.: US 10,445,749 B2
(45) Date of Patent: Oct. 15, 2019

(54) UNIVERSAL CONTENT ARCHITECTURE SYSTEM

(71) Applicant: CERNER INNOVATION, INC., Lenexa, KS (US)

(72) Inventors: Wayne Franklin Basey, Castle Rock, CO (US); Chad Barrett Ruoff, Lee's Summit, MO (US)

(73) Assignee: Cerner Innovation, Inc., Kansas city, KS (US)

( * ) Notice: Subject to any disclaimer, the term of this patent is extended or adjusted under 35 U.S.C. 154(b) by 852 days.

(21) Appl. No.: 13/926,382

(22) Filed: Jun. 25, 2013

(65) Prior Publication Data
US 2014/0379359 A1  Dec. 25, 2014

(51) Int. Cl.
*G06Q 30/02* (2012.01)
*G06F 19/00* (2018.01)

(52) U.S. Cl.
CPC ............ *G06Q 30/02* (2013.01); *G06F 19/32* (2013.01)

(58) Field of Classification Search
CPC ......... G06Q 50/22; G06Q 50/24; G06Q 30/02
See application file for complete search history.

(56) References Cited

U.S. PATENT DOCUMENTS

| | | | |
|---|---|---|---|
| 6,523,019 B1 * | 2/2003 | Borthwick | G06N 20/00 706/45 |
| 7,200,626 B1 * | 4/2007 | Hoang | G06F 11/0751 |
| 2009/0112735 A1 * | 4/2009 | Viehmann | G06Q 30/02 705/26.1 |
| 2009/0150181 A1 * | 6/2009 | Gejdos | G06Q 50/22 705/3 |
| 2014/0244309 A1 * | 8/2014 | Francois | G06Q 10/10 705/3 |

OTHER PUBLICATIONS

Baker, Barbara, John Perry, Robert Jenkins, and Nadezda Nikolova-Kirilova. "A Study of Expanding Prescriptive Authority for Controlled Substances to Advanced Registered Nurse Practitioners (2004 House Bill 595)." Legislative Research Commission, Frankfort, Kentucky. Research.Report No. 323 (2004): 1-122.*

Baker, Barbara, et al. "A Study of Expanding Prescriptive Authority for Controlled Substances to Advanced Registered Nurse Practitioners (2004 House Bill 595)." Legislative Research Commission, Frankfort, Kentucky. Research Report No. 323 (2004): (Year: 2004).*

* cited by examiner

*Primary Examiner* — Robert A Sorey
*Assistant Examiner* — Kristine K Rapillo
(74) *Attorney, Agent, or Firm* — Shook, Hardy & Bacon

(57) ABSTRACT

One or more systems, computer-storage media, and methods are described for receiving, storing, and distributing clinical information to clients subscribed to or granted access to the information. Initially, content packages containing clinical information are received and stored. Datasets are extracted from the content packages and stored. The datasets and content packages are made available to clients via an online marketplace which enables one or more clients to edit, update, or request to merge a plurality of datasets.

20 Claims, 9 Drawing Sheets

UNIVERSAL CONTENT ARCHITECTURE SYSTEM

BACKGROUND

Many clinical care providers consume clinical information on a frequent basis. Oftentimes these clinicians gather clinical information from a plurality of sources, such as, for example, research institutes or electronic medical record (EMR) providers. However, gathering such information is not always a simple task. In particular, many clinicians must learn when new clinical information becomes available, know where to find the information, and independently acquire and review the information. This process may lead to inefficient and inconsistent delivery of medical treatment to patients.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, computer-storage media, and systems for delivering clinical information via an online marketplace to clients subscribed to the information. Content packages are received at a universal content architecture (UCA) system from a plurality of content providers. The content providers may be located globally and/or regionally and the content packages may contain both clinical and non-clinical information. A series of validation steps are taken with respect to the content packages, including, for example, security, structural and content validation steps. Once validated, datasets contained within the content packages are extracted, stored, and published in the online marketplace for client purchase and consumption. Exemplary clients include care providers, healthcare facilities, research and development teams, and the global healthcare community. Exemplary content providers may include regulatory agencies and health records companies. In some embodiments, content providers are clients and vice versa.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for receiving and distributing clinical information to a plurality of clients. In one aspect, a content package is received from a content provider via an online marketplace. The content package may contain one or more datasets of clinical information. The datasets are identified and extracted from the content packages. Two or more extracted datasets, or portions thereof, may be merged together and reformatted to generate a derivative dataset. The datasets, derivative datasets, and content packages are saved, and, depending on the nature and type of information contained therein, may be published in the online marketplace. Once published, clients may log in to the online marketplace, search for and preview the datasets, and purchase or subscribe to information contained within the content packages or datasets.

In another aspect, the present invention is directed to computer-storage media for automatically distributing, via an online marketplace, updated clinical information to one or more clients subscribed to the information. Initially, a content package is received from a first content provider. Upon receiving a request from a client to subscribe to at least a portion of the content package (e.g., a single dataset), the portion of the content package is identified, retrieved and distributed to the client. When the first content provider updates the content package, the updated information may automatically be communicated to the client. Additionally, the updated information may be used to supplement or replace a portion of the content package to which it corresponds.

In yet another aspect, the present invention is directed to a system having a server that distributes clinical information to a client when the client requests the information. The server first receives a request from a client for clinical information published in the online marketplace. Subsequently, the server may determine that the clinical information is stored in a content package or dataset, retrieve the content package or dataset, and distribute the content package or dataset to the client.

Figure 1:
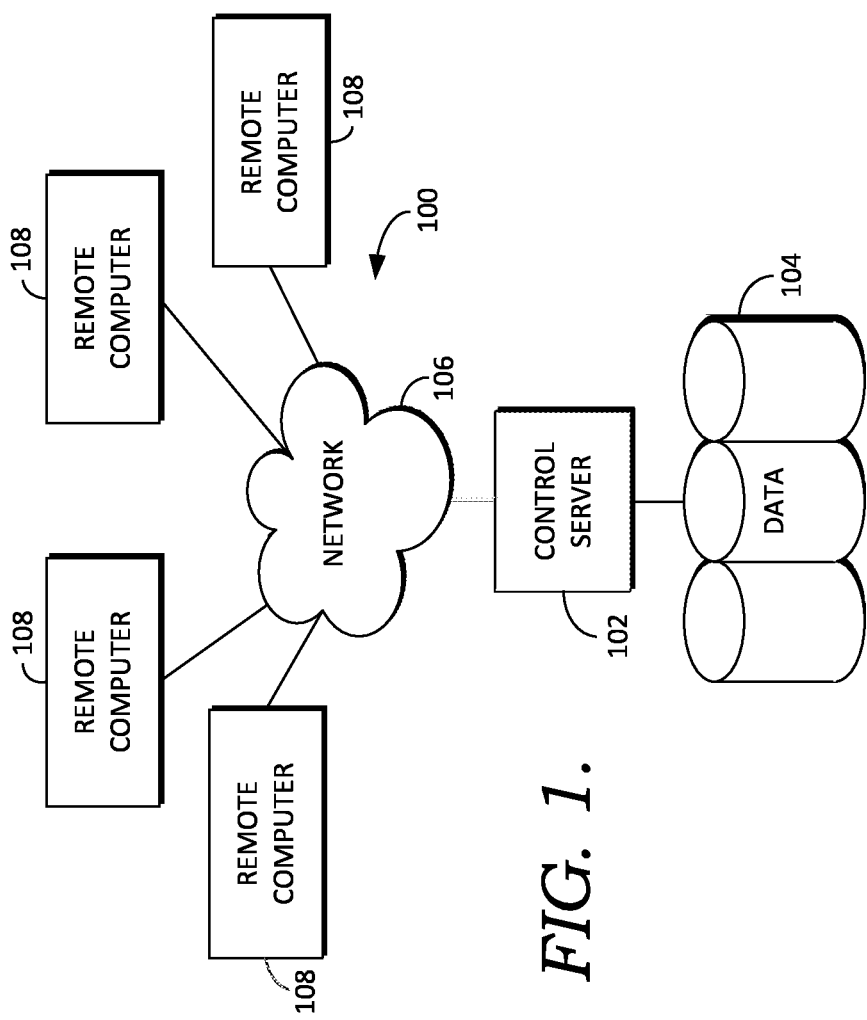
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise non-transitory computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

The computing environment 200 includes a data store 204, a universal architecture system 206, and a computing device 208, all in communication with one another via a network 202. The network 202 may include, without limitation, one or more secure local area networks (LANs) or wide area networks (WANs). The network 202 may be a secure network associated with a facility such as a healthcare facility. The secure network 202 may require that a user log in and be authenticated in order to send and/or receive information over the network 202.

Figure 2:
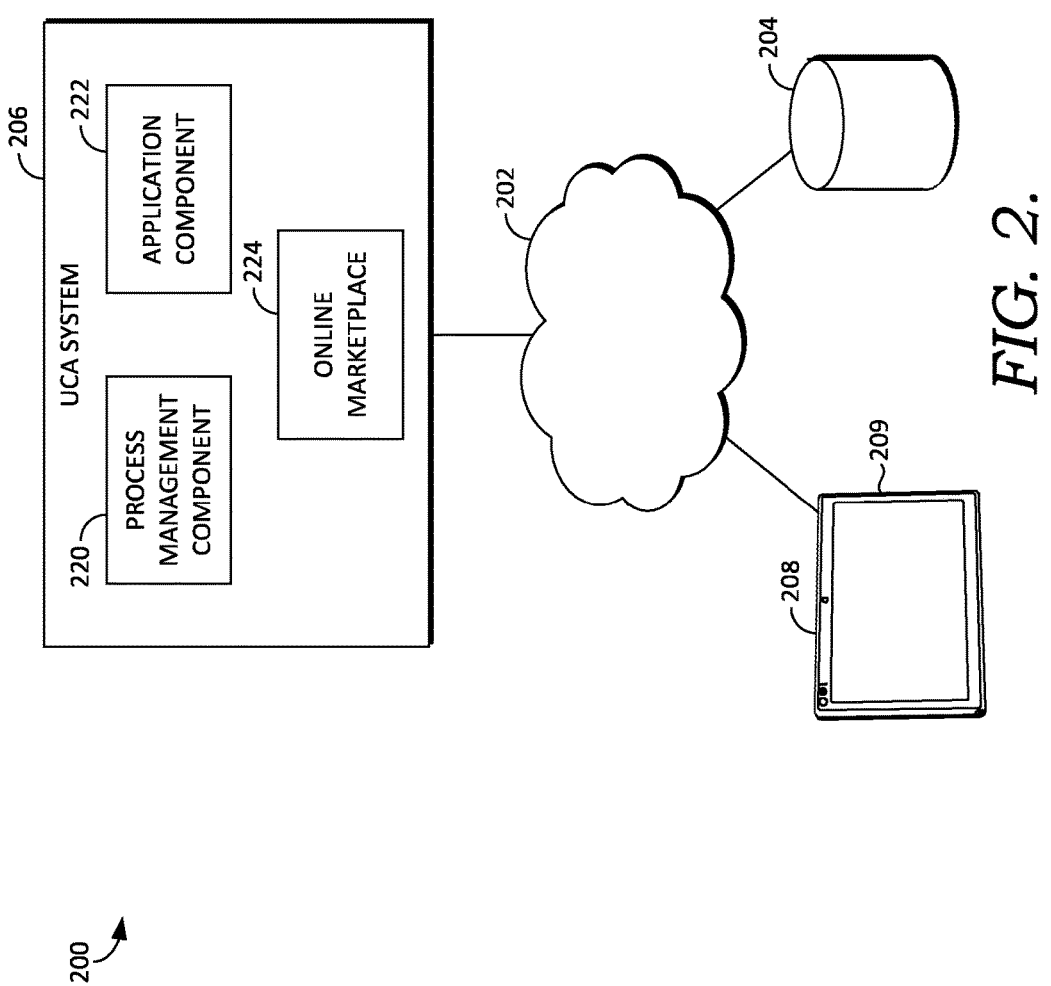
FIG. 2 is a block diagram of an exemplary system for receiving and delivering clinical information to clients, in accordance with an embodiment of the present invention.

In some embodiments, one or more of the illustrated components/modules may be implemented as stand-alone applications. In other embodiments, one or more of the illustrated components/modules may be integrated directly into the operating system of the UCA system 206. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the UCA 206 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 204 is configured to store information for use by, for example, the UCA system 206 and the end-user computing device 208. The information stored in association with the data store 204 is configured to be searchable for one or more items of information stored in association therewith. The information stored in association with the data store 204 may comprise general information used by the UCA system 206 and/or the end-user computing device 208.

In one aspect, the data store 204 is configured to store one or more content packages and/or datasets. A content package is a collection of clinical information, health information, and/or documentation received from a content provider. Content packages may contain one or more datasets, which typically hold smaller amounts of data than the content package. A dataset is formatted as a single table of data, having, for example, columns and rows. Datasets provide a convenient way of retrieving clinical data without downloading an entire content package, which can be very large.

Exemplary information contained in one or both of a content package and dataset may include clinical terminologies, diagnostic code sets, clinical and/or referential data (e.g., drug warnings, side effects, pregnancy warnings, pharmacy and pharmacokinetics information, and the like), coded workflow instructions, discharge instructions, care plans, immunization information, laboratory test result codes, procedure codes, encounter diagnosis codes, and the like. Datasets can contain any arbitrary subset of data from one or more content packages. A dataset may be created and labeled to address the specific needs of a content consumer or consumer group. For example, a dataset may contain a precise subset of the terminology identifiers contained in a content package and a full set of clinical workflow instructions for a regional healthcare facility.

The content and volume of information in the data store 204 are not intended to limit the scope of embodiments of the present invention in any way. Further, though illustrated as a single, independent component, the data store 204 may, in fact, be a plurality of storage devices, for instance, a database cluster, portions of which may reside on the UCA system 206, the end-user computing device 208, and/or any combination thereof.

As shown, the end-user computing device 208 includes the display screen 209. The display screen 209 is configured to display information to a user of the end-user computing device 208. The user of the end-user computing device 208 may include a content provider or a client. Thus, the end-user computing device 208 may display information relevant to communications initiated by and/or received by the end-user computing device 218, such as, for example, graphical user interfaces for uploading content packages to an online marketplace, graphical user interfaces for supplementing or removing content contained in a content package, and graphical user interfaces for purchasing clinical and/or non-clinical information contained in a content package or dataset. Embodiments are not intended to be limited to visual display but rather may also include audio presentation, combined audio/visual presentation, and the like. The end-user computing device 208 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions. Interaction with the display screen 209 of the end-user computing device 208 may be through conventional methods such as a mouse or a touch pad; interaction with the display screen 209 may also occur through the use of gestures such as tapping, swiping, flicking, pinching, and the like.

The computing system environment 200 is merely exemplary. While the UCA system 206 is illustrated as a single unit, it will be appreciated that the UCA system 206 is scalable. For example, the UCA system 206 may in actuality include a plurality of computing devices in communication with one another. Moreover, the data store 204, or portions thereof, may be included within, for instance, the UCA system 206 and the computing device 208 as a computer-storage medium. The single unit depictions are meant for clarity, not to limit the scope of embodiments in any form.

As shown in FIG. 2, the UCA system 206 comprises a process management component 220, an application component 222, and an online marketplace 224. In some embodiments, one or more of the components 220, 222, and 224 may be implemented as stand-alone applications. In other embodiments, one or more of the components 220, 222, and 224 may be integrated directly into the operating system of a computing device such as the remote computer 108 of FIG. 1 or the computing device 208. It will be understood that the components 220, 222, and 224 illustrated in FIG. 2 are exemplary in nature and in number and should not be construed as limiting. Any number of components may be employed to achieve the desired functionality within the scope of embodiments hereof.

The process management component 220 is configured to receive content packages from a plurality of content providers. Upon receiving the content packages, the process management component 220 performs a series of validation steps, including, for example, security, structural and content validation steps. The security validation step ensures that the content packages are safe for storage and distribution within the UCA system 206. For example, the security validation step may include running a virus scan on all files contained within a content package. The structural validation step ensures that all uploaded content packages contain the correct amount of clinical and/or non-clinical information. For example, a structural validation step may involve scanning a content package to make sure that each of ten expected datasets is contained therein. The content validation step ensures that the content package contains the correct type of information. For example, a content package expected to contain prescription drug information will be validated for its inclusion of such information. A content package that fails at any validation step is not published in the online marketplace 224. A notification may also be sent to a content provider when a content package is determined to be deficient in some way.

After validation, the process management component 220 is configured to mine the plurality of content packages stored in the UCA system 206 and extract datasets that comprise the content packages. Each content package and extracted dataset is then stored in the data store 204. The content packages and their extracted datasets may be stored in association with each other. Specifically, each extracted dataset may be stored in association with a computer-usable reference that describes, links to, or identifies the content package from which it was originally extracted.

The process management component 220 is also configured to publish one or more content packages and datasets in the online marketplace 224. Publication may be generally defined as a process of making a content package or dataset available to at least one client via the online marketplace 224. So, for example, a content package or dataset is published when a client can search for, review, preview, purchase or subscribe to the information contained therein.

In some embodiments, the online marketplace 224 enables content providers to select a particular client or group of clients that may purchase and/or edit their content packages and datasets. A content provider may also require, as a condition of submitting a content package to the UCA 206, that the content provider is the only entity with rights to edit the content package. Similarly, content providers may select to publish only a portion of a content packet. For example, a content provider may select to publish only individual datasets, rather than a complete content package.

Additionally, the process management component 220 is configured to merge two or more datasets (or portions thereof), thereby generating a derivative dataset. Datasets may be merged based on requests received from a content provider or client. Datasets may also be automatically merged based on predetermined rules. Derivative datasets may be automatically reformatted to eliminate duplicate information, change an order in which information is presented, replace null or empty field values, and the like. The derivative datasets are stored and, in some embodiments, published in the online marketplace 224. Similarly, the process management component 220 is configured to merge information contained in one or more content packages, thereby generating derivative content packages. The derivative content packages are stored and, in some embodiments, published in the online marketplace 224.

The following example illustrates how a derivative dataset is created and is used for illustrative purposes only. Assume the process management component 220 receives two different content packages. The first content package has a plurality of datasets associated with drug content information. The second content package has at least one dataset associated with drug identifiers. The drug identifiers stored within the second content package satisfy a regulatory Meaningful Use Stage 2 final rule requirement (i.e., the identifiers are properly coded) for medications and medication allergies. To ensure that the first content package meets the regulatory requirement, the process management component 220 automatically extracts and maps the drug identifiers from the second content package to drug information stored in the first content package. The process management component 220 then merges the extracted and mapped information to create a new derivative dataset. For example, the process management component 220 may extract generic drug IDs, drug synonym IDs, and product-level IDs from the first content package, and map such information to MINs (multiple ingredient generic drug IDs), INs (single ingredient generic drug IDs), PINs (precise single ingredient generic drug and salt IDs), and BNs (medication brand name IDs) from the second content package. The extracted information is then merged to create a derivative dataset and may be made available via the online marketplace 224.

The process management component 220 is also configured to activate one or more editorial tools that allow a client or content provider to edit a content package or dataset. In this way, the user (e.g., the client or content provider), via the online marketplace 224, may add, remove, replace, reformat, or take some other action with respect to information stored in a content package or dataset. For example, a content provider may add one or more new rows and columns to a dataset. The edited dataset can then be saved as the most recent version of the dataset and/or as a replacement for the previous version of the dataset.

The process management component 220 is configured to receive a request from a content provider to incorporate updated information into a content package and/or dataset. The client may select the content package or dataset from within the online marketplace 224 via an icon or a link directed to the content package or dataset. The client may also communicate a unique identifier associated with the content package to the UCA system 206. In some embodiments, the identifier is assigned to the content package when the content package is uploaded and subsequently communicated to the client. Once identified, the process management component 220 retrieves the content package or dataset. It then supplements (i.e., adds or appends) the content package or dataset with the updated information, uploads a new version of the content package or dataset (i.e., with updated information already included), or replaces existing portions of the content package or dataset with the updated information. The updated information is then stored as a new version of the content package or dataset (e.g., in association with) or as a replacement for the content package or dataset.

Derivative datasets may also be updated. In one embodiment, a derivative dataset is updated when a user edits or supplements the derivative dataset directly. In another embodiment, a derivative dataset is updated when a user edits or appends one or more fields of an original dataset that form a portion of the derivative dataset. As an example used for illustrative purposes only, assume dataset A and dataset B (and/or portions thereof) were merged to form derivative dataset C. Dataset A is later updated to include 100 new field entries and communicated to the UCA system 206. The 100 new field entries may automatically be mapped to and merged with the corresponding portions of dataset C.

The process management component 220 is also configured to determine that a client is subscribed to a content package or dataset that has recently been updated. Initially, the process management component 220 may determine that a content package or dataset has been updated. It then identifies clients subscribed to the content package or dataset. A client is subscribed to a content package and/or dataset when the client has purchased or been given indefinite or future access to the clinical information contained therein. In one embodiment, the process management component 220 communicates a notification to the client informing the client that an update has been received. The notification may include an identifier that serves to identify the updated content package or dataset. The client can thereafter submit the identifier to the online marketplace 224 or application component 222, and the application component 222 will retrieve and deliver the updated information to the client. As well, in some embodiments, the updated information is communicated automatically to a client subscribed to the updated dataset or content package.

The process management component 220 is also configured to communicate updated information directly to an out-of-system database or electronic system. A supplier of an out-of-system database may request that the process management component 220 add updated information to its out-of-system database directly. Upon receiving the updated information, the process management component 220 communicates the updated information to the out-of-system database, integrates the updated information into the out-of-system database, and reformats the out-of-system database.

The application component 222 is configured to receive a request for clinical information stored in one or more content packages or datasets, retrieve the information, and communicate it to the client via the online marketplace 224 for editing and/or download. In some embodiments, the request includes an identifier that identifies the requested content package and/or dataset. The application component 222 maps the identifier to a content package, retrieves the content package, and distributes it to the requesting client.

The online marketplace 224 is a web application configured to render graphical user interfaces that permit content providers to upload content packages and/or merge or edit content packages or datasets. The online marketplace 224 is configured to enable settings that allow a content provider to restrict publication of their content packages and datasets to one or more clients. Similarly, the online marketplace 224 is configured to enable settings that allow a content provider to set a price or enter into a fee arrangement for distribution of a content package and dataset. In some examples, content providers may set up license agreement terms specifying a period of time that a client has been granted access to a content package or dataset. Content providers may also set up parameters for one-time content downloads, fixed-term access (e.g., from Jan. 1, 2015 to Jan. 1, 2016), and perpetual (i.e., unlimited) content access. The fee arrangements may be fixed or non-fixed.

As explained in greater detail above, the process management component 220 publishes content packages and/or datasets to the online marketplace 224. The online marketplace 224 also receives requests from clients to download, subscribe to and/or view non-restricted content packages and datasets. In one embodiment, the client enters an identifier via the online marketplace 224, and the application component 220 retrieves the content package or dataset associated with the identifier. For example, when a client is notified that a new version of dataset A is available, the client, having a subscription to dataset A, can submit dataset A's identifier to the online marketplace 224. In turn, the application component 220 will locate dataset A, retrieve it, and communicate it to the client. A client may also search for clinical information in the UCA system 206 using filters. Clients can filter results according to, for example, geographic origin, language type, content type, and content provider. For example, a client can set filters to locate clinical information written only in German. A client can also search using keywords. The online marketplace 224 receives the keyword(s), communicates it to the application component 222, and the application component 222 retrieves a list of clinical packages or datasets, which, based on one or more algorithms, are deemed relevant to the keyword search. The retrieved clinical packages and/or datasets are then presented to the client on the end-user computing device 208. Clients can also search for and retrieve portions of content packages (e.g., only two out of ten datasets associated with a content package, including one dataset that relates to drug interactions and one dataset that relates to allergy indications).

Figure 7:
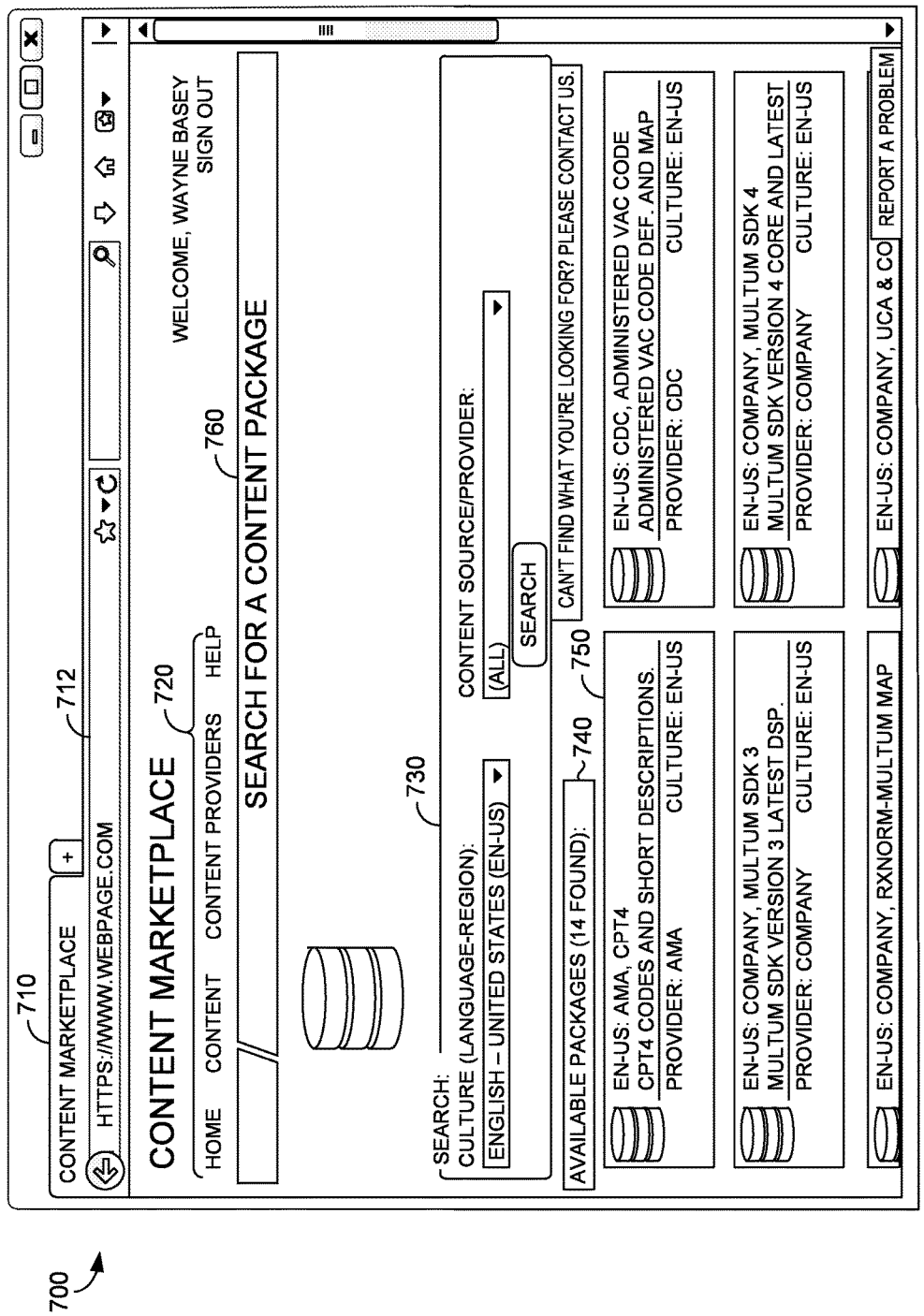
FIG. 7 depicts an exemplary graphical user interface presenting a detailed view of an online marketplace, in accordance with an embodiment of the present invention.

Turning to FIG. 7, FIG. 7 depicts an exemplary graphical user interface (GUI) 700 illustrating a detailed view of an online marketplace page that enables a user to search for and retrieve a content package. The GUI 700 depicts a web browser 710 having a browser toolbar 712 that enables a user to enter a uniform resource locator or a search query to locate and access the online marketplace, such as online marketplace 224 of FIG. 2. The GUI 700 also includes a headings portion 720 that allows a user to select to view another portion of the online marketplace and navigate away from the "search for content package" page 760. As mentioned above, the content package search bar 730 includes a plurality of filters, such as, for example, cultural (e.g., geographic and language) and content provider filters. While not shown, the content package search bar 730 may include a query box that allows a user to perform a keyword search for a content package. The search results portion 740 of GUI 700 may contain a list of search results 750 that satisfy the filter settings or are responsive to the search queries entered by a user in content package search bar 730. Each search result 750 may be presented in association with a cultural origination, name, and brief description of the content package. The search result 750 may also include a content provider name, the size of the content package, and the like.

Figure 8:
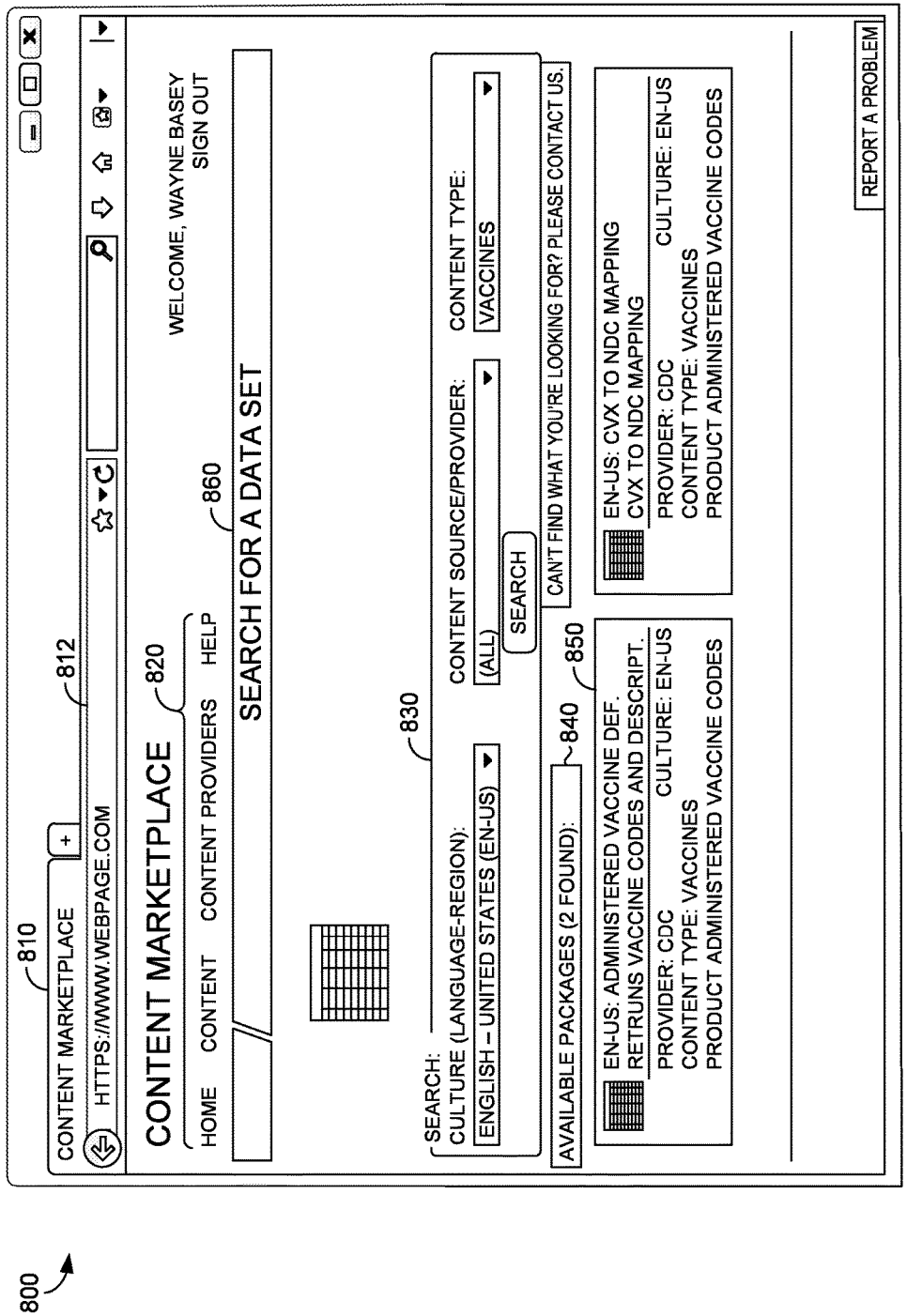
FIG. 8 depicts an exemplary graphical user interface presenting a detailed view of an online marketplace, in accordance with an embodiment of the present invention.

Turning to FIG. 8, FIG. 8 depicts an exemplary graphical user interface (GUI) 800 illustrating a detailed view of an online marketplace page that enables a user to search for and retrieve a dataset. The GUI 800 depicts a web browser 810 having a browser toolbar 812 that enables a user to enter a uniform resource locator or a search query to locate and access the online marketplace, such as online marketplace 224 of FIG. 2. The GUI 800 also includes a headings portion 820 that allows a user to select to view another portion of the online marketplace and navigate away from the "search for dataset" page 860. As mentioned above, there is a dataset search bar 830 that includes a plurality of filters, such as, for example, cultural and content provider filters. While not shown, the dataset search bar 830 may include a query box that allows a user to perform a keyword search for a dataset. The search results portion 840 of GUI 800 may contain a list of search results 850 that satisfy the filter settings or are responsive to the search queries entered by a user in dataset search bar 830. Each search result 850 may be presented in association with cultural origination, content package origination, name, and brief description of the dataset. The search result 850 may also include a content provider name, the size of the dataset, and the like.

Returning to FIG. 2, the online marketplace 224 is configured to render GUIs that permit clients to view summaries of the content packages and datasets to which they are subscribed. The online marketplace 224 is also configured to render GUIs that enable clients to select to view a content package or dataset and/or edit content packages and datasets.

Figure 9:
FIG. 9 depicts an exemplary graphical user interface presenting a detailed view of a subscription page that identifies a subscriber's purchased content packages and datasets, in accordance with an embodiment of the present invention.

Turning to FIG. 9, FIG. 9 depicts an exemplary graphical user interface (GUI) 900 illustrating a detailed view of an online marketplace page that enables a client to view its subscriptions to content packages and datasets. The GUI 900 depicts a web browser 910 having has a browser toolbar 912 that enables a client to enter a uniform resource locator or a search query to locate and access the online marketplace, such as online marketplace 224 of FIG. 2. The "my subscriptions" page 920 contains a content packages portion 930 and a datasets portion 940 that respectively display the client's content package and dataset subscriptions. Exemplary categories used to summarize and identify the content packages and the datasets include culture 950 (e.g., geographic location or language), vendor 952 (e.g. content provider), product 954 (e.g., information type and content), format 956, version 958, published 960 (e.g., publication date), size 962, download link 964 (e.g., link to select to download and/or view the content package), and owner 966 (e.g., client) categories.

Figure 3:
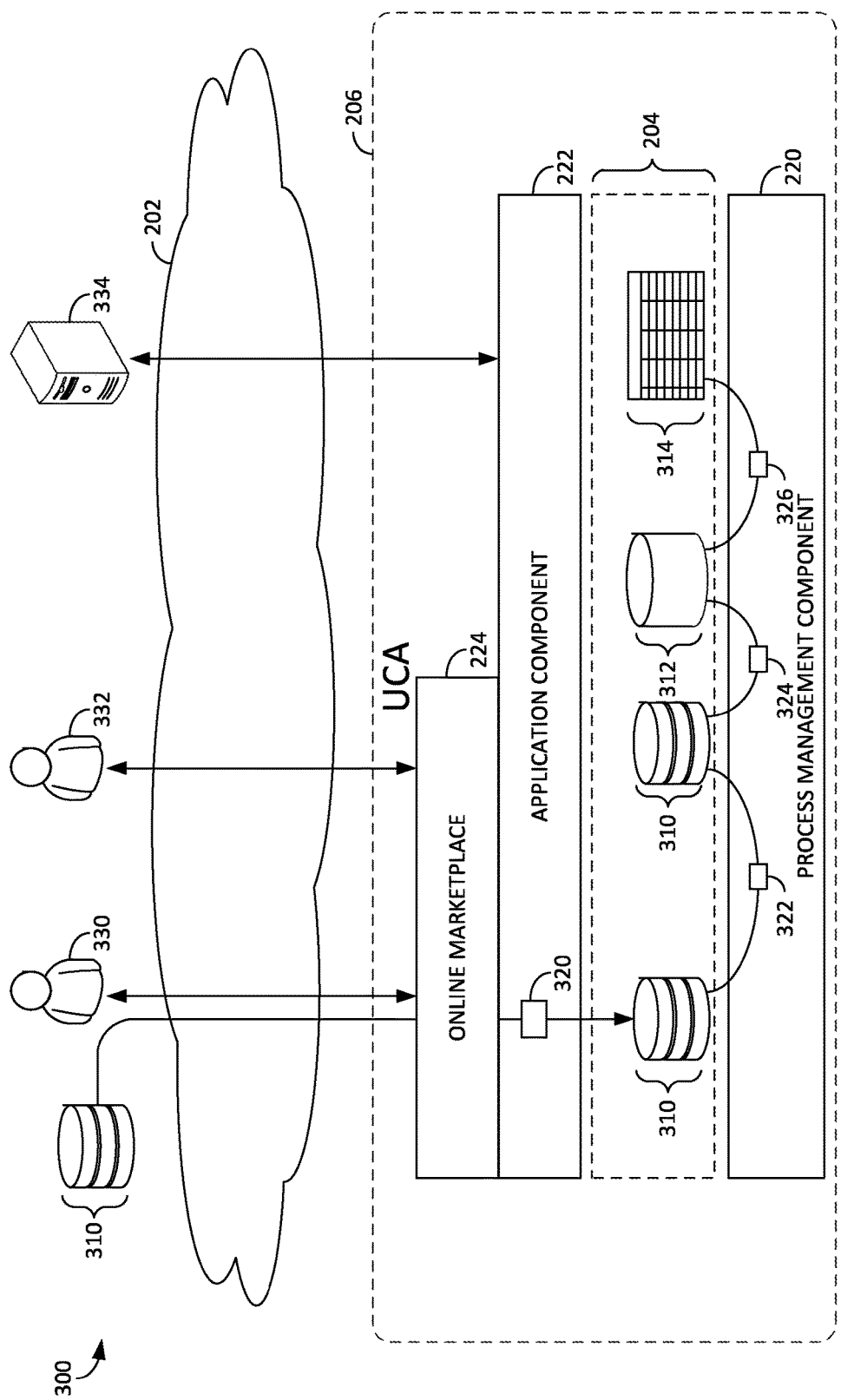
FIG. 3 is an illustrative process-flow diagram that depicts a method of receiving and distributing clinical information to a client, in accordance with an embodiment of the present invention.

Turning to FIG. 3, an illustrative process-flow diagram, labeled generally as 300, is illustrated depicting a method of receiving and distributing clinical information to clients in accordance with an embodiment of the present invention. The process-flow diagram includes a content provider 330, a client 332, and a client 334. In reality, there could be any number of content providers and clients. The content provider 330 and clients 332 and 334 are shown merely as examples. As stated above, a content provider may include a non-human entity, such as an electronic medical record provider or a regulatory agency that collects, generates and/or stores clinical information. A content provider may also include a human entity, such as a physician or hospital administrator. Clients may similarly include human and non-human entities. For example, the client may be computing device having a processor and computer-storage media stored thereon and configured to send a request for and receive clinical information.

At a step 320, a content package 310 is uploaded to a universal content architecture system, such as the UCA system 206 of FIG. 2. The content package 310 is received at the online marketplace 224 (i.e., for manual requests) or the application component 222 (i.e., for automated requests).

At a step 322, the content package 310 is validated. If validated (i.e., at each of the security, content and structural steps), the process management component 220 publishes the content package. At a step 324, a database 312 of clinical information may be extracted from the content package 310. At a step 326, one or more datasets 314 are extracted from the database 324 and stored in the data store 204.

Figure 4:
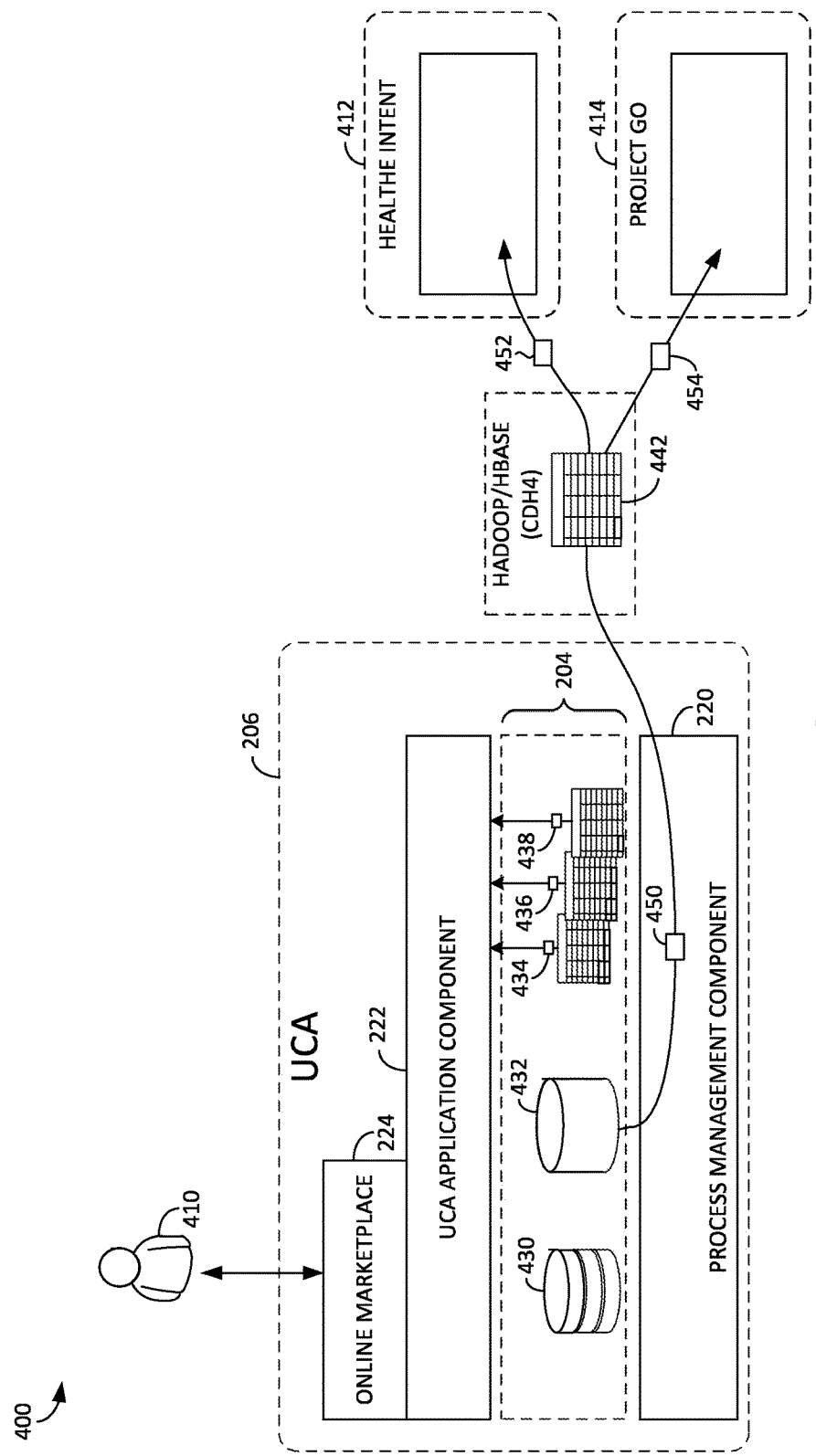
FIG. 4 is an illustrative process-flow diagram that depicts a method of automatically communicating updated clinical information to a client that is subscribed to the information, in accordance with an embodiment of the present invention.

Turning to FIG. 4, an illustrative process-flow diagram, labeled generally as 400, is illustrated depicting a method of automatically communicating updated clinical information to a client that is subscribed to the clinical information in accordance with an embodiment of the present invention. The process-flow diagram includes a client 410, a client 412, and a client 414. The client 410 is a human entity, and the clients 412 and 414 are computer systems and/or non-human entities. The client 410 is subscribed to one or more of the datasets 434, 436, and 438. At a step 460, upon receiving a request (not shown) from client 410, one or more of the datasets 434, 436, and 438 are delivered to the client 410. Similarly, at a step 450, information contained in the database 432, and extracted from content package 430, may be integrated into an out-of-system dataset 442. The information is communicated to the out-of-system dataset 442 directly and fed at steps 452 and 454 to the two separate systems 412 and 414, respectively. The raw data stored in database 432 is integrated into the out-of-system dataset 442 by the process management component 220. In one embodiment, the raw data stored in database 432 is integrated into dataset 442 because the process management component 220 recognizes that the client 412 and 414 are subscribed to the raw data and the raw data is not already stored in the dataset 442.

Figure 5:
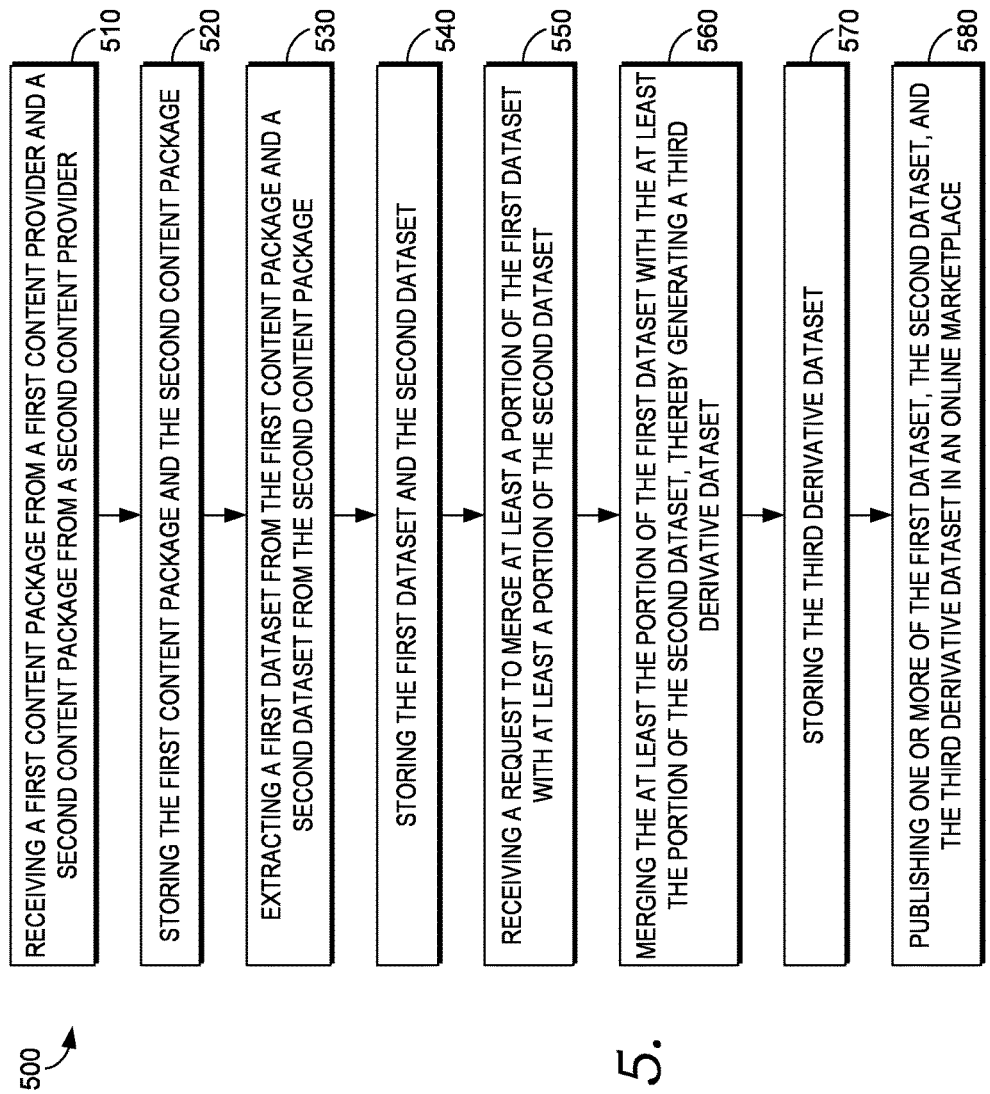
FIG. 5 depicts a flow diagram illustrating a method of facilitating storage and distribution of clinical content packages and datasets, in accordance with an embodiment of the present invention.

Turning to FIG. 5, an illustrative flow diagram, labeled generally as 500, depicts a method of facilitating the storage and distribution of clinical content packages in accordance with an embodiment of the present invention. At a step 510, a first content package and a second content package are received from a first content provider. The first content package may contain a collection of clinical information and documentation, including one or more datasets. The datasets are single tables of data. The first and second content providers may include providers that have authored, generated, collected, and/or uploaded the clinical information. For example, the first content provider may be an electronic health record provider. At a step 520, the first content package and the second content package are stored. At a step 530, a process management server, such as the process management component 220 of FIG. 2, extracts at least a first dataset from the first content package and at least a second dataset from the second content package. At a step 540, the first dataset and the second dataset are stored. At a step 550, a request to merge at least a portion of both the first dataset and the second dataset is received. The request may be received from a client, the first content provider, or second content provider via the online marketplace. In addition, the request may be automated and received at the application component. At a step 560, the portions of the first and the second datasets are merged, thereby generating a third derivative dataset. Although not shown, the third derivative dataset may be reformatted during the merging process. At a step 570, the third derivative dataset is stored. As well, at a step 580, one or more of the first dataset, the second dataset and the third derivative dataset are published in an online marketplace, allowing at least one client access to view, edit, purchase or subscribe to the information contained therein.

Although not shown, additional steps in the method 500 are contemplated. Additional content packages may be received via the online marketplace or an application component, such as application component 222 of FIG. 2. The content packages, including the first and the second content packages, may be stored and published in the online marketplace in association with datasets contained therein or stored and published individually.

As well, a request to purchase or subscribe to information stored in the UCA system 206 of FIG. 2 may be received via the online marketplace. The request may be specific (i.e., it may target a particular dataset) or general (i.e., it may target a type of information expected to be contained in one or more datasets). If the request is specific, the requested content package or dataset is communicated the client. If the request is general, a variety of search results and associated links to datasets and content packages may be returned to the client. At that point, the client may select to view, purchase, subscribe to or edit the desired content package or dataset. Additionally, updated information may be received, determined to correspond to a content package or dataset, and integrated into or saved as a new version of the associated content package or dataset.

Figure 6:
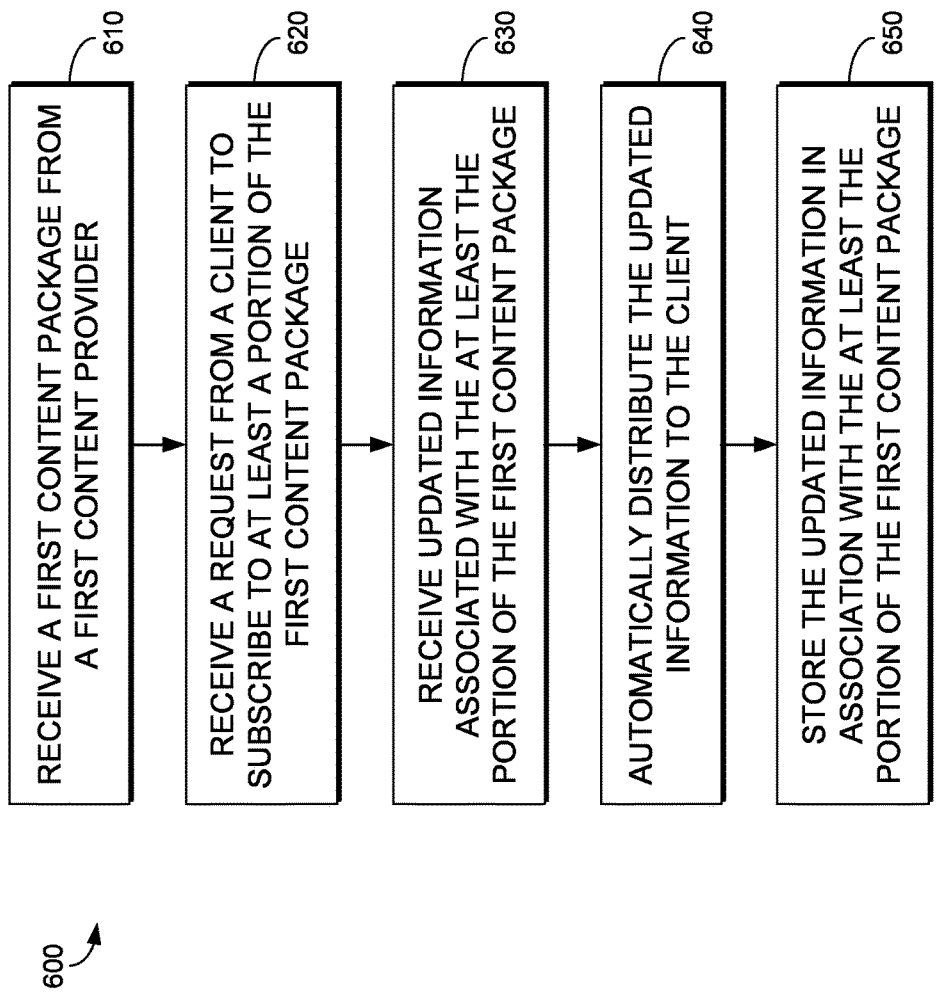
FIG. 6 depicts a flow diagram illustrating a method of automatically distributing clinical information to a client that is subscribed to the information, in accordance with an embodiment of the present invention.

Turning to FIG. 6, a flow diagram labeled generally as 600 depicts a method of automatically distributing updated content package information to a client that is subscribed to the information. At a step 610, a first content package is received from a first content provider. At a step 620, a request from a client to subscribe to at least a portion (e.g., a dataset) of the first content package is received. The client may initiate the request by performing a keyword search, setting filters to narrow search results, and/or submitting an identifier associated with the content package to the online marketplace. In turn, an application server, such as the application component 222 of FIG. 2, retrieves the content package and delivers it to the client. In other embodiments, the application server will automatically integrate updated information into one or more out-of-system datasets belonging to clients subscribed to the information and clients that have granted permission to the UCA to access the out-of-system datasets.

At a step 630, updated information associated with the portion of the first content package may be received from a content provider and/or a client. A process management server, such as the process management server 220 of FIG. 2, recognizes that the updated information has been received. The process management server also recognizes that the client is subscribed to the portion of the content package for which there is now updated information. In response, the updated information is communicated to the client at a step 640. At a step 650, the updated information is stored in association with at least the portion of the first content package.

Embodiments of the invention have been described to be illustrative rather than restrictive. It will be understood that certain features and subcombinations are of utility and may be employed without reference to other features and subcombinations. This is contemplated by and is within the scope of the claims.

The invention claimed is:

1. One or more non-transitory computer-storage media having computer-executable instructions embodied thereon that, when executed by a computing device, cause the computing device to perform a method of generating a regulatory compliant content package the method comprising:

receiving a first content package from a first content provider and a second content package from a second content provider;

performing a structural validation of the first and second content packages that determines the first and second content packages contain a correct number of datasets, and performing a content validation of the first and second content packages that determines the first and second content packages contain a correct type of clinical information, wherein, if the first content package fails the structural validation or the content validation, then a notification that the first content package is deficient is sent to the first content provider and the first content package is not published, and if the second content package fails the structural validation or the content validation, then a notification that the second content package is deficient is sent to the second content provider and the second content package is not published;

based on the first and second content packages passing validation, mining a first dataset from the first content package and a second dataset from the second content package;

associating the first dataset and the second dataset with a computer-usable reference to the first content package and the second content package, respectively, wherein the computer-usable reference links the first dataset to the first content package and the second dataset to the second content package;

extracting identifiers necessary to meet regulatory requirements from the first and second datasets;

merging at least a portion of the first dataset and at least a portion of the second dataset to generate a regulatory compliant content package, the regulatory compliant content package including the identifiers necessary to meet regulatory requirements, wherein merging the portion of the first dataset and the portion of the second dataset includes reformatting the regulatory compliant content package to eliminate duplicate information and replace null field values;

storing the regulatory compliant content package after eliminating the duplicate information and replacing the null field values; and publishing the regulatory compliant content package in an online marketplace.

2. The one or more computer-storage media of claim 1, further comprising:

receiving a request for clinical information from a client via the online marketplace;

determining that the clinical information is stored in the first content package;

extracting the clinical information from the first content package; and distributing the clinical information to the client.

3. The one or more computer-storage media of claim 1, further comprising:

receiving a request from a client to subscribe to information stored within the first content package;

receiving updated information associated with the first content package from the first content provider;

storing the updated information in association with the first content package; and automatically communicating a notification to the client indicating that the updated information has been received.

4. The one or more computer-storage media of claim 3, further comprising:

receiving a request for the updated information from the client; and distributing the updated information to the client.

5. The one or more computer-storage media of claim 4, further comprising:

replacing at least a portion of the first content package with the updated information, thereby generating a new version of the first content package; and publishing the new version of the first content package on the online marketplace.

6. One or more non-transitory computer-storage media having computer-executable instructions embodied thereon that, when executed by a computing device, cause the computing device to perform a method of generating and distributing a regulatory compliant content package to a client that is subscribed to the information, the method comprising:

determining that the client is subscribed to at least a portion of a regulatory compliant content package;

generating the regulatory compliant content package, wherein generating the regulatory compliant content package comprises:

updating a first content package with updated information associated with the first content package received from a first content provider, updating a second content package with updated information associated with the second content package received from a second content provider, performing a structural validation of the updated first content package and the updated second content package, wherein the structural validation determines the updated first and the updated second content packages contain a correct number of datasets, performing a content validation of the updated first content package and the updated second content package, wherein the content validation determines the updated first and the updated second content packages contain a correct type of clinical information, merging at least a portion of the updated first content package and at least a portion of the updated second content package to form a derivative content package, wherein merging the portion of the updated first content package and the portion of the updated second content package includes reformatting the derivative content package to eliminate duplicate information and replace null field values, linking a first dataset to the first content package and linking a second dataset to the second content package with a computer-usable reference, extracting from the updated first content package and the updated second content package identifiers necessary to meet regulatory requirements, and mapping the identifiers necessary to meet regulatory requirements onto the derivative content package, resulting in the regulatory compliant content package;

storing the regulatory compliant content package after eliminating the duplicate information and replacing the null field values; and distributing the regulatory compliant content package to the client.

7. The one or more computer-storage media of claim 6, wherein one or more of the first content package, the second content package, the derivative content package, or the regulatory compliant content package are published in an online marketplace.

8. The one or more computer-storage media of claim 6, wherein the at least the portion of the first content package includes at least one dataset of clinical information associated with the first content package.

9. A system for delivering regulatory compliant content from a content provider to a client, the system comprising:

a computing device associated with an application server and a process management server, the application server and the process management server having one or more processors and one or more computer-storage media; and a data store coupled to the application server, wherein the application server:

receives a request for regulatory compliant clinical information;

determines that the regulatory compliant clinical information is associated with at least a portion of a first content package and at least a portion of a second content package;

performs a structural validation of the first and second content packages that determines the first and second content packages contain a correct number of datasets, and performs a content validation of the first and second content packages that determines the first and second content packages contain a correct type of clinical information;

if the first content package and the second content package are successfully validated based on the structural validation and the content validation, then extract from the first content package and the second content package regulatory compliant identifiers;

maps at least a portion of the first content package and the second content package, including the regulatory identifiers, to a derivative dataset, wherein the derivative dataset comprises the regulatory compliant clinical information requested;

formats the derivative dataset to eliminate duplicate information;

stores the derivative dataset after eliminating the duplicate information;

links the first content package to the derivative dataset and the second content package to the derivative dataset; and provides to the client the derivative dataset comprising the regulatory compliant clinical information.

10. The system of claim 9, wherein the process management server publishes the first content package in an online marketplace.

11. The system of claim 9, wherein the process management server publishes the regulatory compliant clinical information in an online marketplace.

12. The one or more computer-storage media of claim 1, wherein the computing device also performs the step of removing duplicate data from the first content package and the second content package or from the first dataset and the second dataset.

13. The one or more computer-storage media of claim 1, wherein the computing device also performs the step of providing editorial tools to the first content provider, the editorial tools configured to allow the first content provider to edit the first content package or the first dataset.

14. The one or more computer-storage media of claim 1, wherein the first and second content packages are associated with prescription drug information.

15. The one or more computer-storage media of claim 14, wherein the identifiers necessary to meet regulatory requirements are drug identifiers.

16. The one or more computer-storage media of claim 6, wherein the identifiers necessary to meet regulatory requirements comprise one or more of generic drug identifiers, drug synonym identifiers, product-level identifiers, multiple ingredient generic drug identifiers, single ingredient generic drug identifiers, precise single ingredient generic drug and salt identifiers, or medication brand name identifiers.

17. The one or more computer-storage media of claim 6, wherein the computing device also performs the step of receiving a request from a client to subscribe to at least a portion of the regulatory compliant content package.

18. The system of claim 9, wherein the application server further respectively sends a notification of a deficiency to a first content provider associated with the first content package or to a second content provider associated with the second content package if the first content package or the second content package is not successfully validated.

19. The one or more computer-storage media of claim 1, wherein the extracted identifiers are drug identifiers, the drug identifiers including at least one of generic drug identifiers, drug synonym identifiers, or produce level identifiers.

20. The one or more computer-storage media of claim 19, further including mapping the drug identifiers to at least one of multiple ingredient generic drug identifiers, single ingredient generic drug identifiers, precise single ingredient generic drug and salt identifiers, or medication brand name identifiers.

* * * * *

UNITED STATES PATENT AND TRADEMARK OFFICE
CERTIFICATE OF CORRECTION

PATENT NO. : 10,445,749 B2
APPLICATION NO. : 13/926382
DATED : October 15, 2019
INVENTOR(S) : Wayne Franklin Basey et al.

Page 1 of 1

It is certified that error appears in the above-identified patent and that said Letters Patent is hereby corrected as shown below:

In the Claims

Column 13, Line 66: Please remove "package" and replace with --package,--.

Column 16, Line 33: Please remove "extract" and replace with --extracts--.

Signed and Sealed this
Twenty-sixth Day of November, 2019

Andrei Iancu
*Director of the United States Patent and Trademark Office*